US008888839B2

(12) United States Patent
Hansen et al.

(10) Patent No.: US 8,888,839 B2
(45) Date of Patent: Nov. 18, 2014

(54) BIOABSORBABLE STENT AND IMPLANTABLE MEDICAL DEVICE

(71) Applicant: Cook Medical Technologies LLC, Bloomington, IN (US)

(72) Inventors: Palle Munk Hansen, Bjaeverskov (DK); Arne Moelgaard-Neilsen, Copenhagen (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/761,606

(22) Filed: Feb. 7, 2013

(65) Prior Publication Data

US 2013/0204349 A1    Aug. 8, 2013

(30) Foreign Application Priority Data

Feb. 8, 2012   (GB) .................................. 1202173.9

(51) Int. Cl.
| | |
|---|---|
| *A61F 2/06* | (2013.01) |
| *A61F 2/844* | (2013.01) |
| *A61F 2/915* | (2013.01) |
| *A61L 31/14* | (2006.01) |
| *A61F 2/89* | (2013.01) |
| *A61F 2/07* | (2013.01) |

(52) U.S. Cl.
CPC .......... *A61F 2/844* (2013.01); *A61F 2250/0037* (2013.01); *A61F 2/915* (2013.01); *A61L 31/148* (2013.01); *A61F 2/89* (2013.01); *A61F 2002/075* (2013.01); *A61L 31/14* (2013.01); *A61F 2002/91516* (2013.01); *A61F 2230/0067* (2013.01); *A61F 2002/067* (2013.01); *A61F 2250/0031* (2013.01); *A61F 2/07* (2013.01)
USPC ........................ 623/1.38; 623/1.16; 623/23.75

(58) Field of Classification Search
USPC .................. 623/1.38, 1.44, 1.46, 23.75, 1.16
See application file for complete search history.

(56) References Cited

U.S. PATENT DOCUMENTS

| | | |
|---|---|---|
| 5,980,564 A | 11/1999 | Stinson |
| 7,594,928 B2 | 9/2009 | Headley et al. |
| 7,879,367 B2 | 2/2011 | Heublein et al. |
| 2005/0163822 A1 | 7/2005 | Shirahama et al. |
| 2006/0052863 A1 | 3/2006 | Harder et al. |
| 2006/0129222 A1 | 6/2006 | Stinson |
| 2006/0193891 A1 | 8/2006 | Richard |
| 2007/0203564 A1 | 8/2007 | Rusk et al. |
| 2007/0250155 A1 | 10/2007 | Simpson |

FOREIGN PATENT DOCUMENTS

| | | |
|---|---|---|
| EP | 2 186 492 A1 | 5/2010 |
| WO | WO 2005/102220 A1 | 11/2005 |
| WO | WO 2008/156683 | 12/2008 |

OTHER PUBLICATIONS

Combined Search and Examination Report under Sections 17 and 18(3) for GB 1202173.9 mailed Jun. 6, 2012.

*Primary Examiner* — David Isabella
*Assistant Examiner* — Dinah Baria
(74) *Attorney, Agent, or Firm* — Brinks Gilson & Lione (57) ABSTRACT

A stent assembly (10) is formed with a plurality of stent rings (12) which have sections (16, 18, 24) which are of a non-biodegradable material and struts and tie bars (20, 14) which are at least partially biodegradable. The stent ring (12) thus partially biodegrades in a patient over time. The structure is such that the apices (16, 18, 24) of the stent ring (12) are of a non-biodegradable material and thus able to behave as a conventional non-biodegradable stent, that is with the same flexibility and expansion force consistent with such stent rings. Parts (34, 44) of the stent ring (12) will degrade in time, thereby reducing the restoring force produced by the stent ring (12) and reducing the amount of foreign material retained within a patient's body. In one embodiment, the stent ring (12) will separate into individual components after a period.

24 Claims, 5 Drawing Sheets

BIOABSORBABLE STENT AND IMPLANTABLE MEDICAL DEVICE

This application claims the benefit of the filing date of United Kingdom (GB) patent application number 1202173.9, filed Feb. 8, 2012, which is hereby incorporated by reference herein.

TECHNICAL FIELD

The present invention relates to a bioabsorbable stent, which may be either self-expanding or balloon expandable. The invention also relates to an implantable medical device including such a stent, as well as to a method of manufacturing such a stent.

BACKGROUND ART

Stents and other implantable medical devices which incorporate stents are in widespread use in the medical field for dilating patient's vessels, for closing off aneurysms, for treating vascular dissections, for supporting prosthetic elements and so on. Stents have the function of holding the vessel open or for holding a device securely against the vessel wall to effect a good seal as well as to prevent device migration. As a result, it is desirable for the stent to be able to apply a significant opening force and to do so reliably. However, in many instances it is undesirable to maintain pressure against the vessel wall for prolonged periods of time. Long term pressure applied to the vessel wall can cause undesired long term effects such as unnecessary stretching or straightening of the vessel. It is also, in some instances, undesirable to retain long term in a patient's body significant amounts of metal or alloy. These effects can lead to vessel weakening of the vessel and/or stenosis or restenosis.

It is generally undesirable to remove the stent or other medical device from a patient by means of an invasive medical procedure. Attempts have been made, thus, to produce stents which are biodegradable or bioresorbable. While such stents can resolve the problems encountered during the long term use of such implantable medical devices, biodegradable or bioresorbable stents do not generally have the same performance characteristics as stents made purely of metal or metal alloy, resulting in potential loss of efficacy.

Disclosures of biodegradable and bioabsorbable stents can be found, for example, in: US-2005/0163822, U.S. Pat. No. 7,594,928, US-2006/0052863, U.S. Pat. No. 7,879,367, US-2007/0250155, US-2006/0193891, US-2007/0203564, U.S. Pat. Nos. 7,279,005 and 5,980,564.

DISCLOSURE OF THE INVENTION

The present invention seeks to provide an improved stent and implantable medical device incorporating at least one stent, as well as a method of manufacturing such a stent.

According to an aspect of the present invention, there is provided a stent formed as a radially compressible annular ring, said ring including a series of apex portions connected to one another by a series of interconnecting struts; wherein the apex portions are made from a first material being a spring material; and at least one of the struts is formed from or includes a second material being a biodegradable material.

At least one of the struts may be formed from or include a first section of said first material and a second section of a second material, the second material being a biodegradable material. Said first section may be continuous along the length of the strut so as to be unitary with the apex portions. The first section may have a smaller cross-sectional area the apex portions. The first section may be thinner than the apex portions.

In preferred embodiments, once the second material has degraded only the first material of the strut remains. This can result in the strut becoming substantially more flexible than prior to degradation of the second material, and can therefore increase the overall flexibility of the stent ring.

When such a stent is radially compressed, the greatest deflection will tend to occur at the apex portions, which in effect behave as hinges. The struts, normally being substantially straight or just slightly curved, tend not to be flexed or deflected to the same extent as the apex portions and in most cases keep their non-compressed shapes. As a result, the apex portions provide the greatest influence on the expansion pressure generated by the stent. Thus, the performance characteristics in terms of compressibility, expansion and in situ qualities of the stent are most dependent upon the characteristics of the apex portions. The structure of stent taught herein does not lose the characteristics of traditional sprung non-biodegradable stents, yet has the advantage of having a part of the stent biodegrade. Moreover, as the strut or struts degrade, these will either weaken relative to the apex portions so as to flex and thereby reduce the expansion or straightening forces imparted by the stent in situ, or will degrade completely, thereby nullifying the effects of the apex portions. Thus, the teachings herein can provide a stent having the combined qualities of a conventional non-biodegradable stent as well as those of a biodegradable stent.

Advantageously, a plurality of the struts of the stent are or include biodegradable material. Preferably, all of the struts of the stent have this characteristic. The greater number or proportion of struts which are at least partially biodegradable will impart the above qualities to a greater proportion of the stent. Where all of the struts are at least partially biodegradable, the stent will be radially uniform both before and after degradation of the struts In one embodiment, a major portion of the length of the strut or struts is biodegradable, preferably at least 50%, more preferably between 50% to 95%, most preferably between 60% to 80%.

One embodiment has the strut or struts of a layered construction, with a non-biodegradable base layer, preferably of the same material as the apex portions, and at least one layer of a biodegradable material. The biodegradable layer or layers are preferably flush with adjacent surfaces of the apex portions, thereby to present no shoulder or ridge between the different parts of the stent.

In another embodiment, the strut may be biodegradable through the entire of its depth and width, thereby causing the apex portions which it connects to become separated from one another. In this embodiment, the struts may also have transverse dimensions which are equivalent to those of the apex portions of the strut. However, in another embodiment, the struts include or are in the form of a biodegradable coupling sleeve within which arms of the apex portions fit, the sleeves acting to connect together adjacent apex portions to form the stent ring. In this embodiment, the sleeves will typically have a diameter greater than the diameter of the arms, preferably being rounded or tapered to avoid sharp shoulders.

The material forming the apex portions may be of a spring material such as spring steel or of a shape memory material such as a shape memory alloy or polymer. The apex portions may also be made of a balloon expandable material. In the preferred embodiment, the apex portions are made of a nickel and titanium alloy, more preferably of an alloy of nickel, titanium, magnesium and iron. The alloy may also include platinum or other radiopaque material.

An embodiment provides the strut or struts to have a base layer of the same material as the apex portions, preferably an alloy of nickel and titanium with magnesium or iron. The struts and apex sections may also be made substantially entirely of a metal such as magnesium, titanium and iron. The biodegradable layer may be a bioabsorbable polymer. An embodiment provides 70% by volume alloy or metal and 30% by volume bioabsorbable polymer. Other embodiments provide 50% by volume alloy/metal and 50% by volume polymer, and others up to 30% alloy/metal and 70% polymer.

According to another aspect of the present invention, there is provided a stent assembly including a plurality of stent rings as taught herein.

In this aspect, the stent assembly preferably includes a plurality of stent rings arranged serially relative to one another along a common axis, and at least one tie bar tying two adjacent stent rings to one another. Advantageously, the tie bar or bars include or are formed from biodegradable material. It is to be understood that the tie bars could have the same structure as the strut or struts. It is not excluded, though, that the tie bars and struts could have different structures, for instance with the tie bars being made biodegradable through their entire depth/width to separate stent rings and with struts which only partially degrade, or vice versa. Similarly, the tie bars could also have biodegradable sleeves as with the embodiments of stent ring disclosed herein.

According to another aspect of the present invention, there is provided an implantable medical device including at least one stent ring as taught herein. The device could be one of a variety such as but not limited to: a stent assembly, a stent graft, a filter, an occlusion device, a vessel constrictor and the like.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Described below are various embodiments of stent structures which are at least partially biodegradable. The embodiments include one or more stent rings which in the examples shown are in the form of zigzag stents of the Zilver™ type sold by the Applicant. The teachings herein, however, are applicable to stents of a variety of designs, including those having undulating or sinusoidal shapes. Furthermore, even though the embodiments shown are directed to stents and stent grafts, the teachings herein are applicable to any medical device which includes at least one stent ring and in particular in which it is desired to alter the characteristics of the stent ring a period of time after which it has been implanted into a patient. This can include, for instance, vena cava filters, occluders and so on.

The stents are most preferably self-expanding stents, made for instance of a spring material such as spring steel or of a shape memory material such as a shape memory alloy or polymer. It is not excluded, however, that the structure of stent ring and stent assembly taught herein could be used in balloon expandable stents and other medical devices.

The teachings herein enable the provision of a structure of stent which can in situ apply a significant and required expansion force in order deploy the stent effectively in the patient and so as to effect the required medical treatment, yet for the stent to degrade at least partially so that it in time reduces the pressure applied to the vessel wall, thereby to reduce or mitigate adverse long term consequences on the patient. This can be by virtue of the pressure applied by the stent, the amount of stent material, particularly metal, remaining long term within the patient's body and also by permitting long term changes to the vessels, for instance, expansion or elongation of the vessel as the result of growth of the patient. Moreover, the teachings herein can provide a stent with characteristics which are the same as the same as stents which are non-biodegradable, that is which do not suffer from performance losses which can be experienced with biodegradable stents.

The term stent assembly is used herein to denote a stent formed of a plurality of stent rings which are coupled to one another to form a stent. It is to be appreciated that the stent may not necessarily be assembled from separate components as the stent could be manufactured from a single tubing which is cut to form the stent rings and connecting elements.

In the description which follows, mention of biodegradable sections, elements or material is of a first material which degrades relatively quickly, while the other parts or elements, often referred to as non-biodegradable, may be absolutely non-biodegradable or may slowly degrade over an extended period of time. Specifically, it is envisaged that the stent could eventually fully degrade, with the struts and tie bars degrading relatively quickly, in a matter of weeks or months, and the apex portions degrading over a period of several months to a year or a plurality of years. It is to be understood that the term biodegradable encompasses slowly biodegradable structures unless the context intends otherwise.

Figure 1:
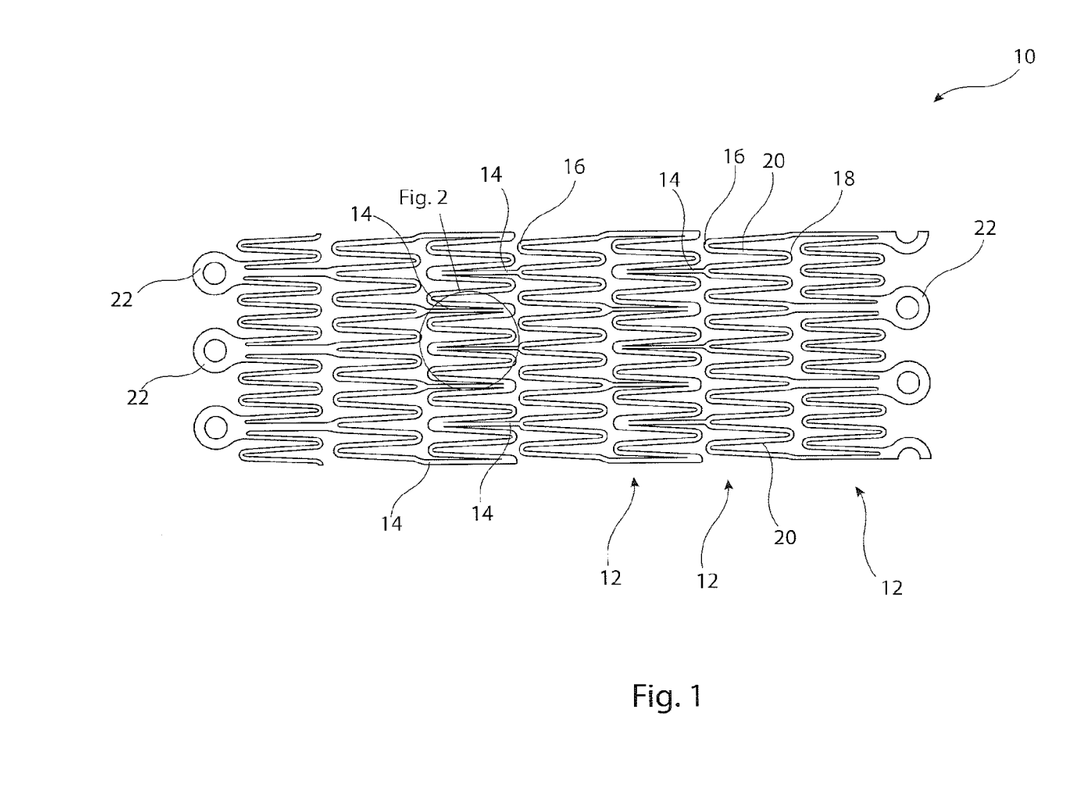
FIG. 1 shows in schematic form an example of a stent assembly in a flattened form.

Referring first to FIG. 1, there is shown an example of a stent assembly 10 in an opened out or flattened configuration. Normally, as is conventional in the art, the stent assembly 10 is wrapped into a cylindrical form with a plurality of stent rings 12 are arranged serially one with respect to the other along the longitudinal direction of the assembly 10 and all with a common centre point or axis. As can be seen in FIG. 1, the stent assembly 10 of this example includes seven stent rings arranged in series, which are interconnected to one another by a plurality of tie bars 14. Each stent ring 12 is formed of a series of apex portions 16, 18 which are coupled together by substantially straight struts 20, in order to form a zigzag undulating shape as shown in the Figure. The stent rings 12 may be produced from a wire bent to shape but may also be cut to shape, for instance from a tubing of raw material.

In the example of FIG. 1, the tie bars 14 extend from the outside of one apex portion 16 of one stent ring 12 to within a corresponding apex portion 16 of the adjacent stent ring 12, in such a manner that the apex portions 16 are all aligned in a series on common lines along the cylindrical axis of the assembly 10, with a similar arrangement for the apex portions 18. This arrangement of stent rings and alignment of the apex portions is only an example and not relevant to the teachings herein.

The example of stent assembly 10 shown in FIG. 1 also includes annular holding rings 22 for holding radiopaque markers, as is known in the art.

Figure 2:
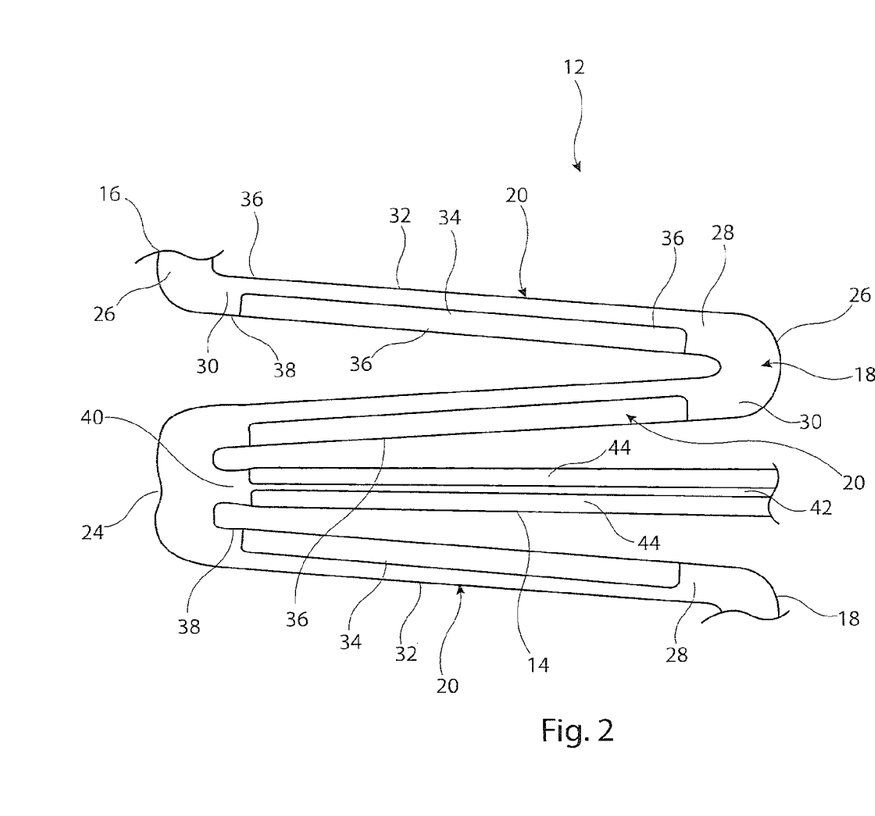
FIG. 2 is an expanded view of a portion of the stent assembly of FIG. 1 showing a part of a stent ring.

Referring now to FIG. 2, there is shown an expanded view of a part of one of the stent rings of the stent of FIG. 1, again in a flattened out condition but as it would be viewed in side elevation in the stent 10. The section of stent ring 12 which can be seen in FIG. 2 has a number of struts 20 coupled to apex portions 16, 18 and 24. Referring first to apex portions 16 and 18, which have the same shape, these have a bent or curved end 26 which terminates in arms 28, 30 which merge into the struts 20. Each end 26 is, in this example, substantially V-shaped, but in other embodiments may be more rounded, for instance when the stent ring is of sinusoidal shape. In this example, the bent or curved end 26 has a greater width than the width of the arms 28, 30 and also of the struts 20, although this is again dependent upon the particular design of stent and its intended medical application.

In this example, the parts 18-24 of the stent 12 are substantially square or rectangular in the cross-section but in other embodiments may be made of a wire of substantially circular or rounded (for instance oval) cross-section.

The struts 20 are, in this embodiment, substantially straight and couple adjacent apex section 16, 18, 24 to one another at the respective arms 28, 30. In this particular example, the material forming the apex sections 16-24 and arms 28, 30 is continuous along the length of the struts 20 so as to be unitary with the sections 26 and of the same non-biodegradable or slowly biodegradable material.

Specifically, the struts 20 are, in this example, formed of two parts, a base layer 32 which is continuous with the arms 28, 30 and ends 16, 18, 24, but which has a width less than the width of the arms 28, as can be seen in FIG. 2. By having a width less than the width of the ends of the arms the base layer 32 therefore has a smaller cross-sectional area than the ends of the arms. The struts 20 also include a second layer 34 which lies alongside the layer 32 and which is made of a biodegradable material. As can be seen in FIG. 2, the biodegradable layer 34 fills what could be described as a gap between opposing arms 28, 30 and takes up the remaining width of the struts 20 such that the side or outer surface 36 of the biodegradable layer 34 is aligned or flush with the corresponding surface 38 of the arms 28, 30. Thus, there is no shoulder or abrupt transition in the outer surface of the stent.

As can be seen in FIG. 2, the biodegradable sections or layers of the struts 20 are, in this example, circumferentially arranged, in other words they do not add to the thickness of the stent structure when viewed in a radial direction of the stent when this is formed into its cylindrical shape. This provides an important characteristic to the stent structure taught herein. More specifically, the bioactive layer or portion 34 will contribute to the stiffness of the strut 20 in the circumferential direction, that is, against radial compression of the stent ring 12. In other words, the biodegradable layer 34 will maintain the strut 20 substantially rigid and thus prompt deflection of the bent/curved ends 16, 18, 24 when the stent ring 12 is radially compressed, for example as it is compressed into an introducer assembly. In some instances, the biodegradable portions of the stent will actually increase the stiffness of those portions as they can be of a stiff and generally inflexible material.

On the other hand, once the layer 34 has degraded, after a period of time such as weeks or months typically, what will remain of the strut 20 is the thin layer or element 32, which will result in the strut 20 becoming substantially more flexible. This will increase the overall flexibility of the stent ring 12 and thus reduce the expansion force generated by the stent ring 12 once compressed and, thereby the expansion force generated by the overall stent assembly 10. In addition, this increase in flexibility increases the fatigue strength of the remaining structure, as it will deform more readily.

As can also be seen in FIG. 2, the stent ring 12 includes a bent or curved end 24 which has provided integral therewith a tie bar 14 which extends from a central arm or extension 40 of the curved end 24 and in practice to the outer curve of a facing apex portion 16 or 18, as will be apparent from FIG. 1. Of course, the locations at which the tie bar 14 couples stent rings 12 together is not relevant to the teachings herein. The tie bar 14 is, in this example, formed of a central layer or section 42 of the same material as that of the curved ends 16, 18, 24, that is of non-biodegradable or slowly biodegradable material. Either side of the central section 42 are layers or zones 44 of biodegradable material, equivalent to the layers 34 of the struts 20. The layers 44 are again flush with the side surfaces of the arms 40 so as to avoid any shoulders or sharp edges.

The biodegradable portions 44 of the tie bars 14 have the same function as the biodegradable sections 34 of the struts 20, that is to make the tie bars 14 relatively rigid during deployment and early implantation of the stent assembly 10 within a patient and then to become more flexible once the biodegradable portions 44 degrade leaving in effect a much thinner tie bar 14. This has the effect of ensuring that the stent assembly 10 has the desired longitudinal strength and rigidity, required particularly during deployment of the stent assembly 10 and early usage thereof, but that the stent assembly 10, upon degradation of the biodegradable portions of the tie bars 14, will become longitudinally much more flexible. This can ensure that the stent assembly 12 will not impart long term a significant straightening force on a vessel within which the stent assembly 10 is implanted.

It will be appreciated that it is not necessary for the tie bars 14 to have two layers of biodegradable material, as they could equally have a single layer of biodegradable material as shown for the struts. Similarly, the struts 20 could have two layers of biodegradable material in a manner akin to the tie bars 14.

It will also be appreciated that the stent rings 12 may have no tie bars 14, in which case they could be directly coupled to one another, such as by having attached opposing apex portions 16, 18. Equally, the stent rings 12 may be separate, that is not tied directly to one another, as may be found for instance in stent grafts and other implantable medical devices.

The portions of material of greater of faster biodegradability, typically referred to as the biodegradable portions, may be in the form of a circumferential covering or sleeve over a base of non-biodegradable or slowly biodegradable material. Similarly, when layered, the layers could be alongside one another, above one another or both, when view from the side elevation.

The non-biodegradable portions of the stent ring 12, in the examples shown the curved ends 16, 18, 24 and layers 32, 42 of the struts 20 and tie bars 14 respectively, may be made of a self-expanding material or of a balloon expandable material. Suitable materials are well known in the art and include, in the case of balloon expandable stents: steel, titanium, nickel and others. Self-expanding stents may be made of spring steel or a shape memory alloy or polymer. In one preferred embodiment, the non-biodegradable portions of stent are made of a shape memory alloy based on nickel and titanium (for instance Nitinol).

More preferably, the self-expanding structure is designed to degrade gradually over time, for instance over a period of months or years. For this purpose, the self-expanding part of the stent may be made of an alloy of nickel and titanium with magnesium or iron. This results in a structure which will slowly biodegrade, typically over a period of many months, one or more years, thereby to result in complete removal of the stent from the patient over time. It has been found that an alloy with such composition provides optimum characteristics to the parts of the stent ring 12 which are intended degrade only slowly, as well as being a good substrate upon which the biodegradable material can be attached. Other embodiments use a self-expanding structure which may be primarily or substantially entirely of a degradable metal, such as magnesium, iron or tungsten. It is to be understood that any biocompatible degradable metal or metal alloy may be used.

The sections 34, 44 of biodegradable material are preferably of a biodegradable polymer, such as: poly-L, D-lactide, poly-L-lactide, poly-D-lactide, bioglass, poly(alpha hydroxy acid), polyglycolic acid, polylactic acid, polycaprolactone, polydioxanone, polyglucanate, polylactic acid-polyelethelene oxide copolymers, tyrosine derived polycarbonate, polyglycolide, modified cellulose, collagen, poly(hydroxybutyrate), polyanhydride, polyphosphoester, poly (amino acids) or combinations thereof.

An embodiment has around 70% by volume alloy/metal and around 30% bioabsorbable polymer. It is envisaged, however, that other embodiments may have 50% alloy/metal and 50% polymer up to about 30% alloy/metal and 70% polymer for stent rings which are majorly biodegradable. These are preferably proportions of the overall stent 10.

The biodegradable layers 34, 44 can be attached directly to the non-biodegradable material but may equally be attached by an adhesive layer or other form of bonding.

As can be seen in FIG. 2, the sections of biodegradable material 34, 44 extend for substantially the entire length of the struts 20 and tie bars 14. This maximises the flexibility of the stent ring and stent assembly once they have biodegraded, and will also substantially reduce the amount of foreign material which will remain within the patient's body long term. Yet, the structure retains the functionality of the apex portions 16, 18 and 24 of the stent ring 12 thus maintaining the performance of the stent ring. The biodegradable sections 34, 44 preferably extend along at least 50% of the length of the struts 20 and tie bars 14, most preferably for at least 50% of their length.

In other embodiments, the zones of biodegradable material 34, 44, could be substantially shorter than shown in FIG. 2 and may extend for just 50% or less of the length of the struts and tie bars.

Figure 3:
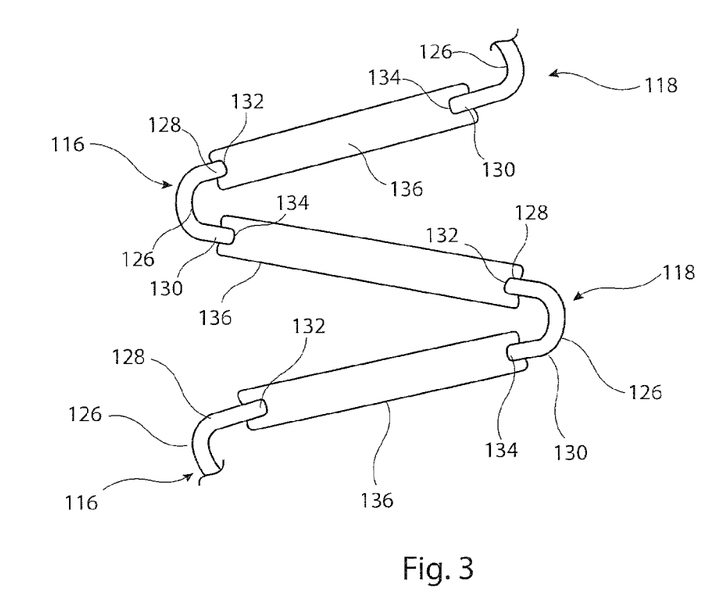
FIG. 3 is a schematic diagram of a part of a stent ring according to another embodiment of the present invention.

Referring now to FIG. 3, there is shown another embodiment of stent ring 112 for the stent assembly 10 of FIG. 1 and, it will be appreciated, usable in other implantable medical devices. The primary distinction between the embodiment of FIG. 3 and the embodiment of FIG. 2 is that the stent ring 112 will, over time, separate into individual components which will be no longer connected to one another. More specifically, the stent ring 112 includes apex sections 116, 118, each having a bent or curved end 126 with, in this embodiment, relatively elongate arms 128, 130. These components 116, 118 of the stent ring 112 are made of a non-biodegradable or slowly biodegradable material. As can be seen in FIG. 3, the elongate arms 128, 130 have ends 132, 134 which face one another but are spaced apart. A connecting sleeve 136, or connectors, (shown in cross-section), overlies the ends 132, 134 of the arms 128, 130 and in effect fixes these relative to one another. The sleeves 136 are made of a biodegradable material, for instance a biodegradable polymer the same as that of the embodiment of FIG. 2. The sleeves 136 are of sufficient strength as to couple together sections 116, 118 of the stent ring 112 to one another to form a unitary stent ring 112 which in practice is able to behave as a stent ring made solely of non-biodegradable material. In other words, the sleeves 136 are preferably substantially rigid. Once the stent ring 112, or medical device of which the stent ring 112 forms a part, is implanted within the vasculature of a patient, the stent ring 112 will typically become bioresorbed into the walls of the vessel, as occurs with most implantable medical devices. The biodegradable sleeves 136 will, on the other hand, degrade and in effect cease to exist as distinct components within the patient, thereby resulting in a separation of the stent portions 116 and 118. As these will be retained by bioresorption in the vessel walls, they will not be free to move within the patient.

The structure of stent ring 112 shown in FIG. 3 has particular advantages in cases where there are likely to be changes to the vessel within which the stent 112 is implanted. This is particularly useful, for instance, in the treatment of younger patients who still have to grow. In these circumstances, a conventional structure of stent or other implantable medical device is not always ideal because of its inability to expand beyond its operating diameter. By contrast, this structure of stent 112 in effect removes the stent 12 in its original condition from within the patient, allowing the patient's vessels to expand and change in shape with growth of the patient, without it being necessary to remove the stent 112 or other implantable medical device from the patient. This can be particularly useful for example, in the treatment of vascular dissections in younger patients.

It will be appreciated that the length of the arms 128, 130 of the bent or curved ends 116, 118 of the stent portions of the stent ring 112 may have lengths other than as shown in FIG. 3. For example, they may be longer so as substantially to abut one another, as they can be shorter to leave a greater gap between their ends 132, 134. Shorter arms 128, 130 result in the retention of less metal alloy or other foreign material within the patient in the long term.

The skilled person will appreciate that the sleeves 136 may take a variety of forms, as long as they retain the function of holding the portions 116, 118 together in such a manner that they can behave as a unitary stent ring.

Figure 4:
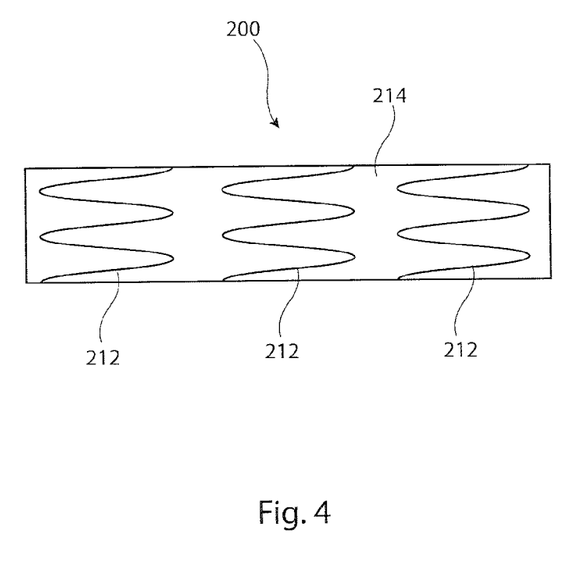
FIG. 4 is a schematic diagram of an example of stent graft.

FIGS. 1, 2 and 3 are directed to stent assemblies. However, the teachings herein are not limited to stent assemblies only. The teachings can for instance be applied to any implantable medical device which uses or includes a stent. Some examples are given in FIGS. 4 and 5. FIG. 4 shows a stent graft 200 provided with a plurality of stent rings 212 attached to a tube of graft material 214. The stent rings 212 may be located on the outside or inside of the graft tube 214 as well as within. One or more of the stent rings 212 may be provided with a structure of the type taught herein, that is with portions which are biodegradable and other portions which are non-biodegradable. The graft material 214 may likewise be made of a biodegradable or bioresorbable material. In the example of FIG. 4, the stent rings 212 are not coupled to one another apart from by means of the graft material 214 but in other embodiments could be connected to one another, for instance by tie bars.

Figure 5:
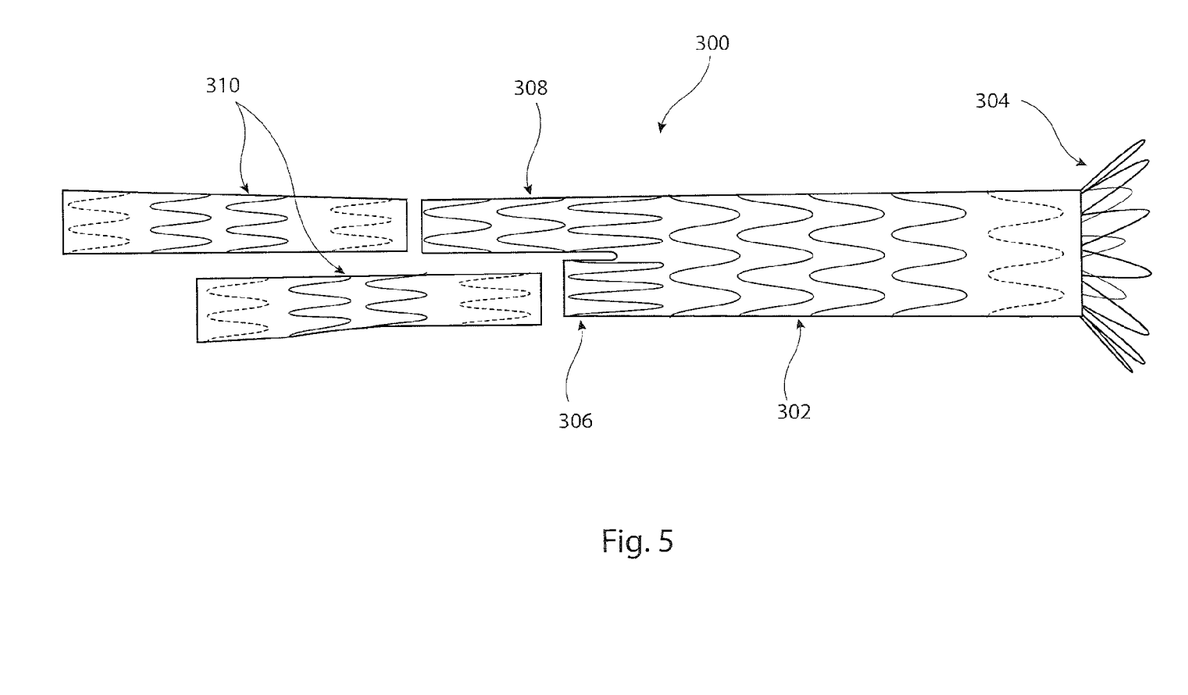
FIG. 5 is a schematic diagram of an example of bifurcated stent graft.

Referring to FIG. 5, there is shown a bifurcated stent graft 300 including a main body portion 203 provided with a flared bare stent 304 at one end and leg portions 306, 308 at the other end. Leg extensions 310 can be coupled to the legs 306, 308.

The stent graft 300 is provided with a plurality of stent rings fixed to or otherwise incorporated in the graft material of the device. One or more of the stent rings of the stent graft 300 may have characteristics as taught herein, that is being partially biodegradable and partially non-biodegradable. Again, as with the example of FIG. 4 the, graft material forming the stent graft 300 may be made of a biodegradable or bioresorbable material. It can equally be made of a bioabsorbable material.

The biodegradable portions of the stent rings and tie bars are preferably such as to degrade after being in the patient for a number of weeks or months, in dependence upon the medical condition and the length of time the stent assembly is to apply opening pressure on the vessel walls. Thus, the stent will apply both at deployment and for this period post deployment a consistent expansion force equivalent to that of a wholly non-biodegradable stent. Upon degradation of the biodegradable portions, the stent will either weaken or separate into individual parts, thereby to reduce the effect of the stent as well as the amount of foreign material which will remain long term in the patient.

The embodiments described above have the biodegradable portions lying alongside the non-biodegradable portions or supports. In other embodiments, the biodegradable portions may overlie or underlie the non-biodegradable portions thus to be radially outside or inside these.

It will be appreciated that although the struts and tie bars forming the stent ring 12, 112 shown particularly in FIGS. 2 and 3 are substantially straight, they could have other shapes, for example to be curved.

It will also be appreciated also that the stent rings 12, 112 disclosed herein may be cut from a sheet of tubular metal but may equally be bent from wires.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The invention claimed is:

1. A stent in the form of a radially compressible annular ring, said ring including a series of apex portions connected to one another by a series of interconnecting struts; wherein the apex portions are made from a first material being a spring material; and at least one of the struts comprises a first section of said first material and a second section of a second material, the second material being a biodegradable material; wherein said first section is continuous along a length of the at least one of the struts so as to be unitary with the apex portions, and wherein the first section has a smaller cross-sectional area than the apex portions.

2. A stent according to claim 1, wherein the first material is substantially non-biodegradable.

3. A stent according to claim 1, wherein the first material is biodegradable at a rate of degradation lower than a rate of degradation of the second material.

4. A stent according to claim 3, wherein the first material degrades at a rate resulting in degradation of the apex portions in a period of months to years.

5. A stent according to claim 1, wherein a plurality of the struts of the stent comprise said second, biodegradable material.

6. A stent according to claim 1, wherein all of the struts of the stent comprise said second, biodegradable material.

7. A stent according to claim 1, wherein the first and second sections are in a circumferential disposition around the stent.

8. A stent according to claim 1, wherein the at least one of the struts is of a layered construction, with the first section being at least one layer of said first material and the second section being at least one layer of said second, biodegradable material.

9. A stent according to claim 1, wherein the second section extends for at least 50% of the length of the at least one of the struts.

10. A stent according to claim 1, wherein the second section extends for at least 75% of the length of the at least one of the struts.

11. A stent according to claim 1, wherein at least 50% of the length of the at least one of the struts is at least partially biodegradable.

12. A stent according to claim 11, wherein between 50% to 95% of the length of the at least one of the struts is at least partially biodegradable.

13. A stent according to claim 12, wherein between 60% to 80% of the length of the at least one of the struts is at least partially biodegradable.

14. A stent according to claim 1, wherein the apex portions are formed from a shape memory material.

15. A stent according to claim 14, wherein the apex portions are made of a nickel and titanium alloy.

16. A stent according to claim 1, wherein the apex portions are made of an alloy of nickel and titanium with magnesium or iron.

17. A stent according to claim 1, wherein the stent is formed of about 30% to about 70% by volume alloy or metal and about 30% to about 70% by volume bioabsorbable polymer.

18. A stent according to claim 1, wherein the at least one of the struts is substantially straight.

19. A stent according to claim 1, wherein the stent is included in at least one of: a stent assembly, a stent graft, a vena cava filter, an occlusion device, and a vascular constrictor.

20. A stent assembly including a plurality of stents, each stent being in the form of a radially compressible annular ring, said ring including a series of apex portions connected to one another by a series of interconnecting struts; wherein the apex portions are made from a first material being a spring material, and at least one of the struts comprises a first section of said first material and a second section of a second material, the second material being a biodegradable material; wherein said first section is continuous along a length of the at least one of the struts so as to be unitary with the apex portions, and wherein the first section has a smaller cross-sectional area than the apex portions, said plurality of stents being coupled to one another.

21. A stent assembly according to claim 20, wherein the stent rings are coupled by tie bars, wherein the tie bars are made at least partially of said second material.

22. A stent assembly according to claim 21, wherein said tie bars include at least one layer of said second material and at least one layer of said first material.

23. A stent assembly according to claim 22, wherein said layers are circumferentially disposed.

24. An implantable medical device including at least one stent, the or each stent being in the form of a radially compressible annular ring, said ring including a series of apex portions connected to one another by a series of interconnecting struts; wherein the apex portions are made from a first material being a spring material, and at least one of the struts comprises a first section of said first material and a second section of a second material, the second material being a biodegradable material; wherein said first section is continuous along a length of the at least one of the struts so as to be unitary with the apex portions, and wherein the first section has a smaller cross-sectional area than the apex portions.

* * * * *